(12) United States Patent
Stein

(10) Patent No.: US 10,219,915 B1
(45) Date of Patent: *Mar. 5, 2019

(54) EXPANDABLE FUSION IMPLANT AND RELATED METHODS

(71) Applicant: NuVasive, Inc., San Diego, CA (US)

(72) Inventor: Christopher Stein, San Diego, CA (US)

(73) Assignee: NuVasive, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/783,977

(22) Filed: Oct. 13, 2017

Related U.S. Application Data

(63) Continuation of application No. 14/285,590, filed on May 22, 2014, now Pat. No. 9,788,971.

(60) Provisional application No. 61/826,299, filed on May 22, 2013.

(51) Int. Cl.
*A61F 2/44* (2006.01)
*A61F 2/30* (2006.01)

(52) U.S. Cl.
CPC .... *A61F 2/447* (2013.01); *A61F 2002/30579* (2013.01)

(58) Field of Classification Search
CPC ...... A61F 2/4455; A61F 2/446; A61F 2/4465; A61F 2/447; A61F 2002/443
See application file for complete search history.

(56) References Cited

U.S. PATENT DOCUMENTS

| | | |
|---|---|---|
| 4,759,769 A | 7/1988 | Hedman et al. |
| 4,863,476 A | 9/1989 | Shepperd |
| 5,554,191 A | 9/1996 | Lahille et al. |
| 5,653,763 A | 8/1997 | Errico et al. |
| 5,658,335 A | 8/1997 | Allen |
| 5,665,122 A | 9/1997 | Kambin |
| 5,669,909 A | 9/1997 | Zdeblick et al. |
| D390,592 S | 2/1998 | Agata |
| 5,776,199 A | 7/1998 | Michelson |
| 5,782,832 A | 7/1998 | Larsen et al. |
| 5,782,919 A | 7/1998 | Zdeblick et al. |
| D397,439 S | 8/1998 | Koros et al. |
| 5,865,848 A | 2/1999 | Baker |
| 5,893,889 A | 4/1999 | Harrington |
| 5,935,129 A | 8/1999 | McDevitt et al. |
| 5,980,522 A | 11/1999 | Koros et al. |
| 6,045,579 A | 4/2000 | Hochshuler et al. |
| 6,080,193 A | 6/2000 | Hochshuler et al. |

(Continued)

FOREIGN PATENT DOCUMENTS

| | | |
|---|---|---|
| AU | 765774 | 3/2002 |
| AU | 2004100977 | 12/2004 |

(Continued)

OTHER PUBLICATIONS

U.S. Appl. No. 14/456,640, Stein et al.

*Primary Examiner* — Si Ming Ku

(74) *Attorney, Agent, or Firm* — NuVasive, Inc.

(57) ABSTRACT

An expandable spinal fusion implant comprising first and second endplates coupled to an expansion member that sits within a housing. The expansion member is translated by a drive mechanism, whereby translation of the expansion member by the drive mechanism in a distal and proximal directions causes the distance between the endplates to increase and decrease, respectively.

18 Claims, 7 Drawing Sheets

(56) References Cited

U.S. PATENT DOCUMENTS

| | | |
|---|---|---|
| 6,102,950 A | 8/2000 | Vaccaro |
| 6,117,174 A | 9/2000 | Nolan |
| 6,129,763 A | 10/2000 | Chauvin et al. |
| 6,176,882 B1 | 1/2001 | Biedermann et al. |
| 6,179,873 B1 | 1/2001 | Zientek |
| 6,190,414 B1 | 2/2001 | Young et al. |
| 6,214,050 B1 | 4/2001 | Huene |
| 6,217,579 B1 | 4/2001 | Koros |
| 6,302,914 B1 | 10/2001 | Michelson |
| H002009 H | 1/2002 | Martin et al. |
| 6,340,369 B1 | 1/2002 | Ferree |
| 6,344,058 B1 | 2/2002 | Ferree |
| 6,350,126 B1 | 2/2002 | Levisman |
| 6,352,557 B1 | 3/2002 | Ferree |
| 6,355,069 B1 | 3/2002 | DeCarlo, Jr. et al. |
| 6,368,351 B1 | 4/2002 | Glenn et al. |
| 6,371,989 B1 | 4/2002 | Chauvin et al. |
| 6,375,655 B1 | 4/2002 | Zdeblick et al. |
| 6,419,702 B1 | 7/2002 | Ferree |
| 6,436,140 B1 | 8/2002 | Liu et al. |
| 6,436,142 B1 | 8/2002 | Paes et al. |
| 6,443,989 B1 | 9/2002 | Jackson |
| 6,443,990 B1 | 9/2002 | Aebi et al. |
| 6,447,544 B1 | 9/2002 | Michelson |
| 6,447,547 B1 | 9/2002 | Michelson |
| 6,451,057 B1 | 9/2002 | Chen et al. |
| 6,454,806 B1 | 9/2002 | Cohen et al. |
| 6,454,807 B1 | 9/2002 | Jackson |
| 6,471,724 B2 | 10/2002 | Zdeblick et al. |
| 6,478,823 B1 | 11/2002 | Michelson |
| 6,491,724 B1 | 12/2002 | Ferree |
| 6,506,051 B2 | 1/2003 | Levisman |
| 6,520,991 B2 | 2/2003 | Huene |
| 6,533,791 B1 | 3/2003 | Betz et al. |
| 6,562,074 B2 | 5/2003 | Gerbec et al. |
| 6,576,016 B1 | 6/2003 | Hochshuler et al. |
| 6,579,290 B1 | 6/2003 | Hardcastle et al. |
| 6,613,091 B1 | 9/2003 | Zdeblick et al. |
| 6,613,093 B2 | 9/2003 | DeCarlo, Jr. et al. |
| 6,641,614 B1 | 11/2003 | Wagner et al. |
| 6,645,206 B1 | 11/2003 | Zdeblick et al. |
| 6,648,917 B2 | 11/2003 | Gerbec et al. |
| 6,648,918 B2 | 11/2003 | Ferree |
| 6,666,891 B2 | 12/2003 | Boehm, Jr. et al. |
| 6,685,742 B1 | 2/2004 | Jackson |
| 6,695,851 B2 | 2/2004 | Zdeblick et al. |
| 6,706,070 B1 | 3/2004 | Wagner et al. |
| 6,719,796 B2 | 4/2004 | Cohen et al. |
| 6,719,797 B1 | 4/2004 | Ferree |
| 6,730,126 B2 | 5/2004 | Boehm, Jr. et al. |
| 6,733,535 B2 | 5/2004 | Michelson |
| 6,743,255 B2 | 6/2004 | Ferree |
| 6,773,460 B2 | 8/2004 | Jackson |
| 6,821,298 B1 | 11/2004 | Jackson |
| 6,835,206 B2 | 12/2004 | Jackson |
| 6,852,129 B2 | 2/2005 | Gerbec et al. |
| 6,863,673 B2 | 3/2005 | Gerbec et al. |
| 6,905,512 B2 | 6/2005 | Paes et al. |
| 6,955,691 B2 | 10/2005 | Chae et al. |
| 7,066,961 B2 | 6/2006 | Michelson |
| 7,070,598 B2 | 7/2006 | Lim et al. |
| 7,087,055 B2 | 8/2006 | Lim et al. |
| 7,128,760 B2 | 10/2006 | Michelson |
| 7,156,874 B2 | 1/2007 | Paponneau et al. |
| 7,204,853 B2 | 4/2007 | Gordon et al. |
| 7,211,112 B2 | 5/2007 | Baynham et al. |
| 7,217,291 B2 | 5/2007 | Zucherman et al. |
| 7,217,293 B2 | 5/2007 | Branch, Jr. |
| 7,220,280 B2 | 5/2007 | Kast et al. |
| 7,238,186 B2 | 7/2007 | Zdeblick et al. |
| 7,282,063 B2 | 10/2007 | Cohen et al. |
| 7,316,714 B2 | 1/2008 | Gordon et al. |
| 7,410,501 B2 | 8/2008 | Michelson |
| 7,431,735 B2 | 10/2008 | Liu et al. |
| 7,445,636 B2 | 11/2008 | Michelson |
| 7,503,933 B2 | 3/2009 | Michelson |
| 7,547,308 B2 | 6/2009 | Bertagnoli et al. |
| 7,569,074 B2 | 8/2009 | Eisermann et al. |
| 7,588,599 B2 | 9/2009 | Sweeney |
| 7,618,458 B2 | 11/2009 | Biedermann et al. |
| 7,621,951 B2 | 11/2009 | Glenn et al. |
| 7,621,958 B2 | 11/2009 | Zdeblick et al. |
| 7,655,043 B2 | 2/2010 | Peterman et al. |
| 7,655,046 B2 | 2/2010 | Dryer et al. |
| 7,678,148 B2 | 3/2010 | Peterman |
| 7,703,727 B2 | 4/2010 | Selness |
| 7,704,279 B2 | 4/2010 | Moskowitz et al. |
| 7,708,778 B2 | 5/2010 | Gordon et al. |
| 7,722,674 B1 | 5/2010 | Grotz |
| 7,727,280 B2 | 6/2010 | McLuen |
| 7,731,751 B2 | 6/2010 | Butler et al. |
| 7,749,270 B2 | 7/2010 | Peterman |
| 7,749,279 B2 | 7/2010 | Twomey et al. |
| 7,753,958 B2 | 7/2010 | Gordon et al. |
| 7,758,644 B2 | 7/2010 | Trieu |
| 7,763,028 B2 | 7/2010 | Lim et al. |
| 7,771,473 B2 | 8/2010 | Thramann |
| 7,785,351 B2 | 8/2010 | Gordon et al. |
| 7,789,914 B2 | 9/2010 | Michelson |
| 7,794,480 B2 | 9/2010 | Gordon et al. |
| 7,799,081 B2 | 9/2010 | McKinley |
| 7,799,082 B2 | 9/2010 | Gordon et al. |
| 7,819,921 B2 | 10/2010 | Grotz |
| 7,824,445 B2 | 11/2010 | Biro et al. |
| 7,828,848 B2 | 11/2010 | Chauvin et al. |
| 7,828,849 B2 | 11/2010 | Lim |
| 7,837,734 B2 | 11/2010 | Zucherman et al. |
| 7,846,188 B2 | 12/2010 | Moskowitz et al. |
| 7,846,206 B2 | 12/2010 | Oglaza et al. |
| 7,850,733 B2 | 12/2010 | Baynham et al. |
| 7,875,034 B2 | 1/2011 | Josse et al. |
| 7,875,078 B2 | 1/2011 | Wysocki et al. |
| 7,879,098 B1 | 2/2011 | Simmons, Jr. |
| 7,909,869 B2 | 3/2011 | Gordon et al. |
| 7,931,688 B2 | 4/2011 | Landry et al. |
| 7,942,903 B2 | 5/2011 | Moskowitz et al. |
| 7,951,180 B2 | 5/2011 | Moskowitz et al. |
| 7,972,363 B2 | 7/2011 | Moskowitz et al. |
| 7,985,258 B2 | 7/2011 | Zdeblick et al. |
| 8,021,430 B2 | 9/2011 | Michelson |
| 8,025,665 B2 | 9/2011 | Lim et al. |
| 8,052,723 B2 | 11/2011 | Gordon et al. |
| 8,062,375 B2 | 11/2011 | Glerum et al. |
| 8,080,041 B2 | 12/2011 | Boehm, Jr. et al. |
| 8,097,035 B2 | 1/2012 | Glenn et al. |
| 8,105,358 B2 | 1/2012 | Phan |
| 8,105,382 B2 | 1/2012 | Olmos et al. |
| 8,118,870 B2 | 2/2012 | Gordon et al. |
| 8,118,871 B2 | 2/2012 | Gordon et al. |
| 8,123,810 B2 | 2/2012 | Gordon et al. |
| 8,128,700 B2 | 3/2012 | Delurio et al. |
| 8,147,550 B2 | 4/2012 | Gordon et al. |
| 8,172,903 B2 | 5/2012 | Gordon et al. |
| 8,187,332 B2 | 5/2012 | McLuen |
| 8,221,501 B2 | 7/2012 | Eisermann et al. |
| 8,221,502 B2 | 7/2012 | Branch, Jr. |
| 8,241,331 B2 | 8/2012 | Arnin |
| 8,257,370 B2 | 9/2012 | Moskowitz et al. |
| 8,257,440 B2 | 9/2012 | Gordon et al. |
| 8,262,666 B2 | 9/2012 | Baynham et al. |
| 8,262,736 B2 | 9/2012 | Michelson |
| 8,267,966 B2 | 9/2012 | McCormack et al. |
| 8,273,129 B2 | 9/2012 | Baynham et al. |
| 8,303,601 B2 | 11/2012 | Bandeira et al. |
| 8,303,658 B2 | 11/2012 | Peterman |
| 8,308,804 B2 | 11/2012 | Krueger |
| 8,317,025 B1 | 11/2012 | Kolozs et al. |
| 8,317,866 B2 | 11/2012 | Palmatier et al. |
| 8,328,818 B1 | 12/2012 | Seifert et al. |
| 8,337,562 B2 | 12/2012 | Landry et al. |
| 8,353,913 B2 | 1/2013 | Moskowitz et al. |
| 8,361,152 B2 | 1/2013 | McCormack et al. |
| 8,366,777 B2 | 2/2013 | Matthis et al. |
| 8,377,071 B2 | 2/2013 | Lim et al. |

(56) References Cited

U.S. PATENT DOCUMENTS

| | | |
|---|---|---|
| 8,382,842 B2 | 2/2013 | Greenhalgh et al. |
| 8,398,713 B2 | 3/2013 | Weiman |
| 8,403,990 B2 | 3/2013 | Dryer et al. |
| 8,419,795 B2 | 4/2013 | Sweeney |
| 8,425,558 B2 | 4/2013 | McCormack et al. |
| 8,435,298 B2 | 5/2013 | Weiman |
| 8,435,299 B2 | 5/2013 | Chauvin et al. |
| 8,444,696 B2 | 5/2013 | Michelson |
| 8,444,697 B1 | 5/2013 | Butler et al. |
| 8,460,389 B2 | 6/2013 | DeLurio et al. |
| 8,480,748 B2 | 7/2013 | Poulos |
| 8,491,657 B2 | 7/2013 | Attia et al. |
| 8,496,706 B2 | 7/2013 | Ragab et al. |
| 8,506,635 B2 | 8/2013 | Palmatier et al. |
| 8,512,348 B2 | 8/2013 | Chabansky et al. |
| 8,512,407 B2 | 8/2013 | Butler et al. |
| 8,518,114 B2 | 8/2013 | Marik |
| 8,518,120 B2 | 8/2013 | Glerum et al. |
| 8,523,946 B1 | 9/2013 | Swann |
| 8,545,567 B1 | 10/2013 | Krueger |
| 8,556,975 B2 | 10/2013 | Lechoslaw et al. |
| 8,556,979 B2 | 10/2013 | Glerum et al. |
| 8,562,683 B2 | 10/2013 | McKinley |
| 8,568,481 B2 | 10/2013 | Olmos et al. |
| 8,574,300 B2 | 11/2013 | McManus et al. |
| 8,579,907 B2 | 11/2013 | Lim et al. |
| 8,579,980 B2 | 11/2013 | DeLurio et al. |
| 8,579,981 B2 | 11/2013 | Lim et al. |
| 8,597,360 B2 | 12/2013 | McLuen et al. |
| 8,603,168 B2 | 12/2013 | Gordon et al. |
| 8,623,054 B2 | 1/2014 | McCormack et al. |
| 8,623,091 B2 | 1/2014 | Suedkamp et al. |
| 8,628,578 B2 | 1/2014 | Miller et al. |
| 8,641,767 B2 | 2/2014 | Landry et al. |
| 8,641,769 B2 | 2/2014 | Malandain |
| 8,647,386 B2 | 2/2014 | Gordon et al. |
| 8,685,095 B2 | 4/2014 | Miller et al. |
| 8,696,720 B2 | 4/2014 | Lazarof |
| 8,702,798 B2 | 4/2014 | Matthis et al. |
| 8,709,086 B2 | 4/2014 | Glerum |
| 8,734,516 B2 | 5/2014 | Moskowitz et al. |
| 8,747,444 B2 | 6/2014 | Moskowitz et al. |
| 8,753,345 B2 | 6/2014 | McCormack et al. |
| 8,753,347 B2 | 6/2014 | McCormack et al. |
| 8,753,377 B2 | 6/2014 | McCormack et al. |
| 8,753,398 B2 | 6/2014 | Gordon et al. |
| 8,778,025 B2 | 7/2014 | Ragab et al. |
| 8,784,450 B2 | 7/2014 | Moskowitz et al. |
| 8,790,407 B2 | 7/2014 | Chauvin et al. |
| 8,795,366 B2 | 8/2014 | Varela |
| 8,828,062 B2 | 9/2014 | McCormack et al. |
| 8,828,066 B2 | 9/2014 | Lazarof |
| 8,834,472 B2 | 9/2014 | McCormack et al. |
| 8,845,731 B2 | 9/2014 | Weiman |
| 8,845,732 B2 | 9/2014 | Weiman |
| 8,845,734 B2 | 9/2014 | Weiman |
| 8,852,279 B2 | 10/2014 | Weiman |
| 8,858,638 B2 | 10/2014 | Michelson |
| 8,864,833 B2 | 10/2014 | Glerum et al. |
| 8,870,959 B2 | 10/2014 | Arnin |
| 8,888,853 B2 | 11/2014 | Glerum et al. |
| 8,888,854 B2 | 11/2014 | Glerum et al. |
| 8,894,652 B2 | 11/2014 | Seifert et al. |
| 8,894,711 B2 | 11/2014 | Varela |
| 8,894,712 B2 | 11/2014 | Varela |
| 8,906,099 B2 | 12/2014 | Poulos |
| 8,920,507 B2 | 12/2014 | Malandain |
| 8,926,701 B2 | 1/2015 | De Lurio et al. |
| 8,926,704 B2 | 1/2015 | Glerum et al. |
| 8,940,048 B2 | 1/2015 | Butler et al. |
| 8,968,406 B2 | 3/2015 | Arnin |
| 8,968,408 B2 | 3/2015 | Schaller et al. |
| 8,974,534 B2 | 3/2015 | Krueger |
| 8,986,389 B2 | 3/2015 | Lim et al. |
| 8,992,621 B2 | 3/2015 | Chauvin et al. |
| 8,998,992 B2 | 4/2015 | Seifert et al. |
| 9,005,293 B2 | 4/2015 | Moskowitz et al. |
| 9,011,492 B2 | 4/2015 | McCormack et al. |
| 9,034,040 B2 | 5/2015 | Seifert et al. |
| 9,034,041 B2 | 5/2015 | Wolters et al. |
| 9,039,771 B2 | 5/2015 | Glerum et al. |
| 9,055,985 B2 | 6/2015 | Lazarof |
| 9,078,769 B2 | 7/2015 | Farin |
| 9,095,446 B2 | 8/2015 | Landry et al. |
| 9,101,488 B2 | 8/2015 | Malandain |
| 9,119,730 B2 | 9/2015 | Glerum et al. |
| 9,125,757 B2 | 9/2015 | Weiman |
| 9,138,277 B2 | 9/2015 | Fitzpatrick |
| 9,149,364 B2 | 10/2015 | McManus et al. |
| 9,180,017 B2 | 11/2015 | Poulos |
| 9,186,262 B2 | 11/2015 | McLuen et al. |
| 9,192,484 B2 | 11/2015 | Landry et al. |
| 9,204,974 B2 | 12/2015 | Glerum et al. |
| 9,211,196 B2 | 12/2015 | Glerum et al. |
| 9,216,095 B2 | 12/2015 | Glerum et al. |
| 9,233,007 B2 | 1/2016 | Sungarian et al. |
| 9,271,846 B2 | 3/2016 | Lim et al. |
| 9,283,089 B2 | 3/2016 | McKay |
| 9,301,854 B2 | 4/2016 | Moskowitz et al. |
| 9,320,610 B2 | 4/2016 | Alheidt et al. |
| 9,320,615 B2 | 4/2016 | Suedkamp et al. |
| 9,351,848 B2 | 5/2016 | Glerum et al. |
| 9,358,123 B2 | 6/2016 | McLuen et al. |
| 9,358,126 B2 | 6/2016 | Glerum et al. |
| 9,358,128 B2 | 6/2016 | Glerum et al. |
| 9,358,129 B2 | 6/2016 | Weiman |
| 9,398,961 B2 | 7/2016 | Malandain |
| 9,408,707 B2 | 8/2016 | Oglaza et al. |
| 9,408,708 B2 | 8/2016 | Greenhalgh |
| 9,414,936 B2 | 8/2016 | Miller et al. |
| 9,445,856 B2 | 9/2016 | Seifert et al. |
| 9,445,919 B2 | 9/2016 | Palmatier et al. |
| 9,452,063 B2 | 9/2016 | Glerum et al. |
| 9,486,324 B2 | 11/2016 | Hochschuler et al. |
| 9,492,287 B2 | 11/2016 | Glerum et al. |
| 9,510,954 B2 | 12/2016 | Glerum et al. |
| 9,510,955 B2 | 12/2016 | Marino et al. |
| 9,526,627 B2 | 12/2016 | Tabor et al. |
| 9,526,628 B2 | 12/2016 | Krueger |
| 9,532,821 B2 | 1/2017 | Moskowitz et al. |
| 9,539,108 B2 | 1/2017 | Glerum et al. |
| 9,545,319 B2 | 1/2017 | Farin |
| 9,549,824 B2 | 1/2017 | McAfee |
| 9,566,168 B2 | 2/2017 | Glerum et al. |
| 9,579,124 B2 | 2/2017 | Gordon et al. |
| 9,579,215 B2 | 2/2017 | Suedkamp et al. |
| 9,592,131 B2 | 3/2017 | Sandstrom et al. |
| 9,597,200 B2 | 3/2017 | Glerum et al. |
| 9,603,713 B2 | 3/2017 | Moskowitz et al. |
| 9,622,791 B2 | 4/2017 | McCormack et al. |
| 9,622,875 B2 | 4/2017 | Moskowitz et al. |
| 9,629,665 B2 | 4/2017 | McCormack et al. |
| 9,642,712 B2 | 5/2017 | Schaller et al. |
| 9,655,747 B2 | 5/2017 | Glerum et al. |
| 9,662,223 B2 | 5/2017 | Matthis et al. |
| 9,675,385 B2 | 6/2017 | Moskowitz et al. |
| 9,675,469 B2 | 6/2017 | Landry et al. |
| 2002/0040243 A1 | 4/2002 | Attali et al. |
| 2002/0045945 A1 | 4/2002 | Liu et al. |
| 2002/0161444 A1 | 10/2002 | Choi |
| 2002/0165613 A1 | 11/2002 | Lin et al. |
| 2003/0135279 A1 | 7/2003 | Michelson |
| 2004/0087947 A1 | 5/2004 | Lim et al. |
| 2004/0133280 A1 | 7/2004 | Trieu |
| 2004/0254643 A1 | 12/2004 | Jackson |
| 2005/0107878 A1 | 5/2005 | Conchy |
| 2005/0171541 A1 | 8/2005 | Boehm, Jr. et al. |
| 2005/0192669 A1 | 9/2005 | Zdeblick et al. |
| 2005/0203625 A1 | 9/2005 | Boehm, Jr. et al. |
| 2005/0278036 A1 | 12/2005 | Leonard et al. |
| 2005/0283245 A1 | 12/2005 | Gordon et al. |
| 2006/0069436 A1 | 3/2006 | Sutton et al. |
| 2006/0095136 A1 | 5/2006 | McLuen |
| 2006/0122701 A1 | 6/2006 | Kiester |

(56) References Cited

U.S. PATENT DOCUMENTS

| | | |
|---|---|---|
| 2006/0195192 A1 | 8/2006 | Gordon et al. |
| 2006/0229729 A1 | 10/2006 | Gordon et al. |
| 2006/0241764 A1 | 10/2006 | Michelson |
| 2006/0241774 A1 | 10/2006 | Attali et al. |
| 2007/0050030 A1 | 3/2007 | Kim |
| 2007/0073406 A1 | 3/2007 | Gordon et al. |
| 2007/0270954 A1 | 11/2007 | Wu |
| 2008/0021559 A1 | 1/2008 | Thramann |
| 2008/0051902 A1 | 2/2008 | Dwyer |
| 2008/0147193 A1* | 6/2008 | Matthis .......... A61F 2/4465 623/17.16 |
| 2008/0183204 A1 | 7/2008 | Greenhalgh et al. |
| 2009/0043394 A1 | 2/2009 | Zdeblick et al. |
| 2009/0198241 A1 | 8/2009 | Phan |
| 2009/0198245 A1 | 8/2009 | Phan |
| 2009/0198338 A1 | 8/2009 | Phan |
| 2009/0299478 A1 | 12/2009 | Carls et al. |
| 2010/0023057 A1 | 1/2010 | Aeschlimann et al. |
| 2010/0049325 A1 | 2/2010 | Biedermann et al. |
| 2010/0070041 A1 | 3/2010 | Peterman et al. |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0234952 A1 | 9/2010 | Peterman |
| 2010/0241231 A1 | 9/2010 | Marino et al. |
| 2010/0249933 A1 | 9/2010 | Trieu |
| 2010/0286780 A1 | 11/2010 | Dryer et al. |
| 2011/0015742 A1 | 1/2011 | Hong |
| 2011/0029086 A1 | 2/2011 | Glazer et al. |
| 2011/0137349 A1 | 6/2011 | Moskowitz et al. |
| 2011/0208312 A1 | 8/2011 | Moskowitz et al. |
| 2011/0218627 A1 | 9/2011 | Rampersaud et al. |
| 2011/0238184 A1 | 9/2011 | Zdeblick et al. |
| 2012/0058451 A1 | 3/2012 | Lazarof |
| 2012/0059472 A1 | 3/2012 | Weiman |
| 2012/0059481 A1 | 3/2012 | Abernathie et al. |
| 2012/0109319 A1 | 5/2012 | Perisic |
| 2012/0197405 A1 | 8/2012 | Cuevas et al. |
| 2012/0245691 A1 | 9/2012 | Reimels |
| 2012/0277861 A1 | 11/2012 | Steele et al. |
| 2012/0330419 A1 | 12/2012 | Moskowitz et al. |
| 2012/0330421 A1 | 12/2012 | Weiman |
| 2013/0013070 A1 | 1/2013 | McCormack et al. |
| 2013/0018468 A1 | 1/2013 | Moskowitz et al. |
| 2013/0018469 A1 | 1/2013 | Moskowitz et al. |
| 2013/0023991 A1 | 1/2013 | Moskowitz et al. |
| 2013/0023992 A1 | 1/2013 | Moskowitz et al. |
| 2013/0053962 A1 | 2/2013 | Moskowitz et al. |
| 2013/0103153 A1 | 4/2013 | Blackwell et al. |
| 2013/0103154 A1 | 4/2013 | Trieu et al. |
| 2013/0110168 A1 | 5/2013 | McCormack et al. |
| 2013/0110248 A1 | 5/2013 | Zipnick |
| 2013/0116791 A1 | 5/2013 | Theofilos |
| 2013/0144388 A1 | 6/2013 | Emery et al. |
| 2013/0178940 A1 | 7/2013 | Farley |
| 2013/0204371 A1 | 8/2013 | McLuen et al. |
| 2013/0231747 A1 | 9/2013 | Olmos et al. |
| 2013/0297028 A1 | 11/2013 | Zipnick |
| 2013/0297029 A1 | 11/2013 | Kana et al. |
| 2013/0310935 A1 | 11/2013 | Swann |
| 2014/0107790 A1 | 4/2014 | Combrowski |
| 2014/0249629 A1 | 9/2014 | Moskowitz et al. |
| 2014/0296916 A1 | 10/2014 | McCormack et al. |
| 2015/0081021 A1 | 3/2015 | Ciupik |
| 2015/0094814 A1 | 4/2015 | Emerick et al. |
| 2015/0105824 A1 | 4/2015 | Moskowitz et al. |
| 2015/0216518 A1 | 8/2015 | McCormack et al. |
| 2015/0230931 A1 | 8/2015 | Greenhalgh |
| 2015/0230934 A1 | 8/2015 | Chauvin et al. |
| 2015/0374507 A1 | 12/2015 | Wolters et al. |
| 2016/0008040 A1 | 1/2016 | McCormack et al. |
| 2016/0015527 A1 | 1/2016 | McManus et al. |
| 2016/0015529 A1 | 1/2016 | Reimels |
| 2016/0030191 A1 | 2/2016 | McLuen et al. |
| 2016/0058579 A1 | 3/2016 | Aeschlimann et al. |
| 2016/0135961 A1 | 5/2016 | Aeschlimann et al. |
| 2016/0143748 A1 | 5/2016 | Lim et al. |
| 2016/0193056 A1 | 7/2016 | McKay |
| 2016/0213482 A1 | 7/2016 | Alheidt et al. |
| 2016/0242932 A1 | 8/2016 | McLuen et al. |
| 2016/0296340 A1 | 10/2016 | Gordon et al. |
| 2016/0302943 A1 | 10/2016 | Oglaza et al. |
| 2016/0310291 A1 | 10/2016 | Greenhalgh |
| 2016/0317315 A1 | 11/2016 | Weiman |
| 2016/0324659 A1 | 11/2016 | Malandain |
| 2016/0324661 A1 | 11/2016 | Miller et al. |
| 2016/0354131 A1 | 12/2016 | Seifert et al. |
| 2016/0374826 A1 | 12/2016 | Palmatier et al. |
| 2016/0374830 A1 | 12/2016 | Moskowitz et al. |
| 2017/0035468 A1 | 2/2017 | McCormack et al. |
| 2017/0035576 A1 | 2/2017 | Schaller et al. |
| 2017/0086986 A1 | 3/2017 | McAfee |
| 2017/0119539 A1 | 5/2017 | Glerum et al. |
| 2017/0119540 A1 | 5/2017 | Greenhalgh |
| 2017/0119541 A1 | 5/2017 | Greenhalgh |
| 2017/0119542 A1 | 5/2017 | Logan et al. |
| 2017/0119546 A1 | 5/2017 | Farin |
| 2017/0128229 A1 | 5/2017 | Suedkamp et al. |
| 2017/0165083 A1 | 6/2017 | Greenhalgh |

FOREIGN PATENT DOCUMENTS

| | | |
|---|---|---|
| AU | 2011203582 | 8/2011 |
| CA | 1337842 | 1/1996 |
| CA | 2447257 | 12/1996 |
| CN | 2668075 | 1/2005 |
| CN | 1621015 | 6/2005 |
| CN | 2730336 | 10/2005 |
| CN | 201861800 | 4/2006 |
| CN | 101268963 | 9/2008 |
| CN | 202191381 | 4/2012 |
| CN | 202235781 | 5/2012 |
| CN | 203001182 | 6/2013 |
| CN | 103356310 | 10/2013 |
| DE | 4012622 | 7/1991 |
| DE | 4416605 | 6/1995 |
| DE | 10241948 | 4/2004 |
| DE | 102005033608 | 1/2007 |
| DE | 102010004133 | 9/2011 |
| DE | 102012203256 | 9/2013 |
| EP | 0635246 | 1/1995 |
| EP | 0880950 | 12/1998 |
| EP | 1290985 | 3/2003 |
| EP | 1382315 | 1/2004 |
| EP | 1532949 | 5/2005 |
| EP | 1541096 | 6/2005 |
| EP | 1889587 | 2/2008 |
| EP | 2213263 | 8/2010 |
| EP | 2226039 | 9/2010 |
| EP | 2510904 | 10/2012 |
| ES | 2067421 | 3/1995 |
| ES | 2099008 | 5/1997 |
| FR | 2707477 | 1/1995 |
| FR | 2708192 | 2/1995 |
| FR | 2717068 | 9/1995 |
| FR | 2803741 | 7/2001 |
| FR | 2815845 | 5/2002 |
| FR | 2866228 | 8/2005 |
| FR | 2866229 | 8/2005 |
| FR | 2874814 | 3/2006 |
| FR | 2943529 | 10/2010 |
| FR | 2943530 | 10/2010 |
| FR | 2981261 | 4/2013 |
| JP | 2005137418 | 6/2005 |
| JP | 2008054710 | 3/2008 |
| JP | 2008126085 | 6/2008 |
| KR | 20010112139 | 12/2001 |
| KR | 20020025647 | 4/2002 |
| KR | 100410823 | 1/2003 |
| KR | 20030012142 | 2/2003 |
| KR | 20040064577 | 7/2004 |
| KR | 20050064501 | 6/2005 |
| KR | 20080001064 | 1/2008 |
| KR | 20080042341 | 5/2008 |

(56) References Cited

FOREIGN PATENT DOCUMENTS

| | | |
|---|---|---|
| KR | 100953930 | 4/2010 |
| KR | 20120119812 | 10/2012 |
| KR | 20130082281 | 7/2013 |
| RU | 2063730 | 7/1996 |
| RU | 2210343 | 8/2003 |
| RU | 105157 | 6/2011 |
| RU | 2460499 | 9/2012 |
| RU | 131611 | 8/2013 |
| SU | 988281 | 1/1983 |
| SU | 1424826 | 9/1988 |
| WO | WO9000037 | 1/1990 |
| WO | WO9531158 | 11/1995 |
| WO | WO9700054 | 1/1997 |
| WO | WO9926562 | 6/1999 |
| WO | WO200074605 | 12/2000 |
| WO | WO200392507 | 11/2003 |
| WO | WO2004012634 | 2/2004 |
| WO | WO2006081843 | 8/2006 |
| WO | WO2006117463 | 11/2006 |
| WO | WO2006134262 | 12/2006 |
| WO | WO2007009107 | 1/2007 |
| WO | WO2007028706 | 3/2007 |
| WO | WO2008132322 | 11/2008 |
| WO | WO2009064787 | 5/2009 |
| WO | WO2010148112 | 12/2010 |
| WO | WO2011142761 | 11/2011 |
| WO | WO2012031267 | 3/2012 |
| WO | WO2013152257 | 10/2013 |

\* cited by examiner

EXPANDABLE FUSION IMPLANT AND RELATED METHODS

CROSS REFERENCE TO RELATED APPLICATIONS

This application is a continuation of U.S. patent application Ser. No. 14/285,590, filed May 22, 2014, now U.S. Pat. No. 9,788,971, which claims the benefit of the filing date of U.S. Provisional Application No. 61/826,299, which was filed on May 22, 2013. The contents of U.S. Provisional Application No. 61/826,299 are incorporated by reference in their entirety as part of this application.

BACKGROUND

This application relates to an expandable spinal fusion implant for use in spinal surgery.

SUMMARY

To reduce risk of neural injury, the device will have the ability to be implanted to an intervertebral disc space in a collapsed state and expanded to a desired height. Expansion will be accomplished by translating an expansion mechanism mated to the inferior and superior endplates. In addition a large aperture at the proximal end of the device allows for post packing of bone graft material into the hollow interior of the device, which is in communication with a fusion aperture in each of the superior and inferior endplates. In order to have the large through aperture at the proximal end of the device, the drive mechanism is offset from the width centerline of the device.

The device includes a housing, expansion mechanism, support rails, superior endplate, inferior endplate, endplate retainer, endplate safety retainer, drive mechanism, and drive mechanism retainer.

The expansion mechanism rides on rails that are retained partially in both the housing and expansion mechanism. There is one rail on each of the two lateral sides of the device. The expansion mechanism has ramps that are on the superior and inferior sides at both the distal and proximal ends. The ramps on the superior side mate with the superior endplate and the ramps on the inferior side mate with the inferior endplate. The expansion member includes a hollow interior for receiving bone graft material and for allowing bone growth therethrough. The hollow interior of the expansion mechanism is in communication with fusion apertures in each of the superior and inferior endplates.

To achieve expansion and contraction the endplates must be fixed in the longitudinal direction during translation of the expansion mechanism. An endplate retainer housed within the distal end of the housing mates with both the superior and inferior endplates and prohibits translation of the endplates, but allows for expansion.

The expansion mechanism is translated by advancing the drive mechanism, which is retained within the proximal end of the housing and offset from the width centerline. This offset allows for the large through cannula and post packing of bone graft material. The drive mechanism is mated to the expansion mechanism with the drive mechanism retainer. Advancement of the drive mechanism toward the distal end of the device allows the endplates to expand, while the withdrawal of the drive mechanism toward the proximal end of the device results in contraction of the endplates.

An endplate safety retainer located in the expansion mechanism prohibits the removal of the superior and inferior endplates from the expansion mechanism. Superior and inferior in flat and lordotic configurations are contemplated for use with the device described herein.

DETAILED DESCRIPTION

Figure 1:
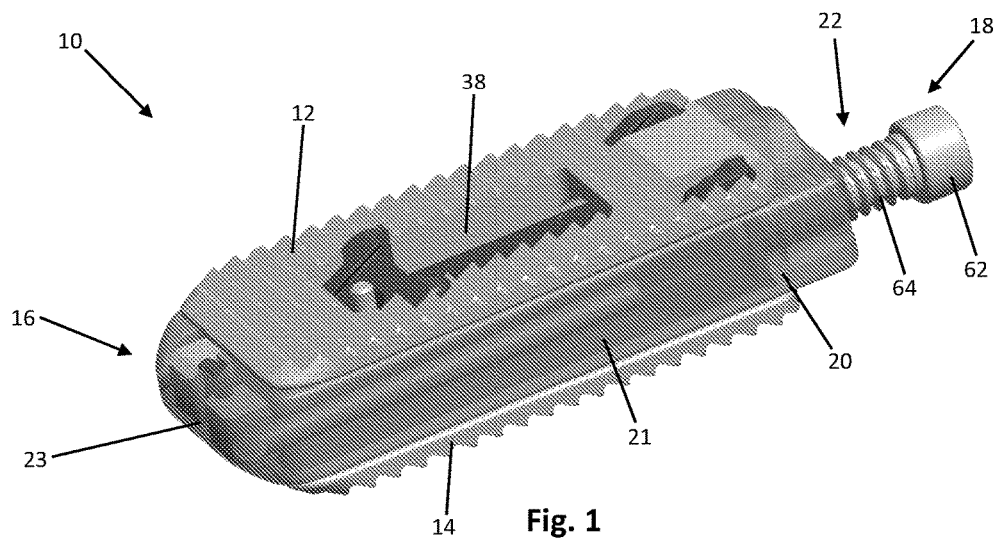
FIG. 1 is a perspective view of an exemplary embodiment of an expandable spinal fusion implant in its collapsed state.
Figure 2:
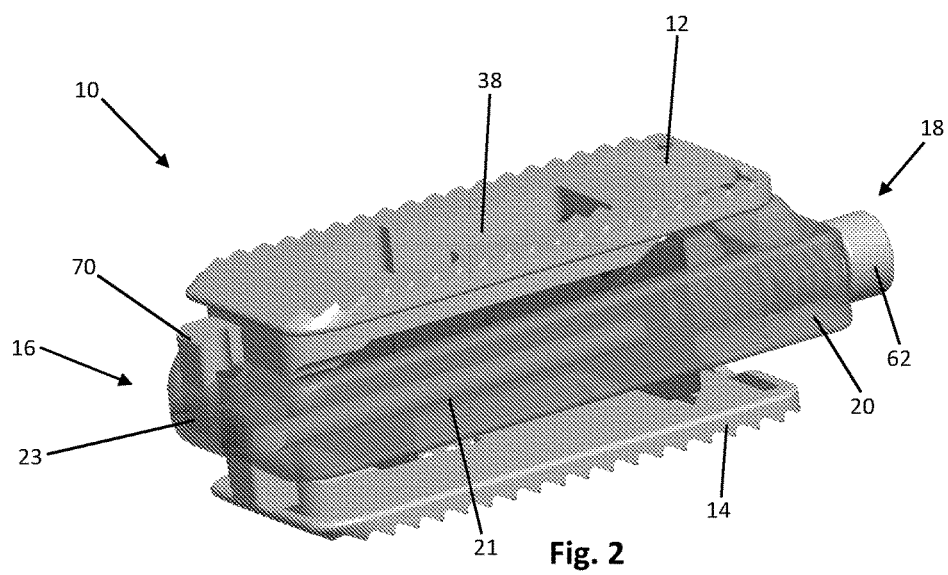
FIG. 2 is a perspective view of the expandable spinal fusion implant of FIG. 1 in its expanded state.
Figure 3:
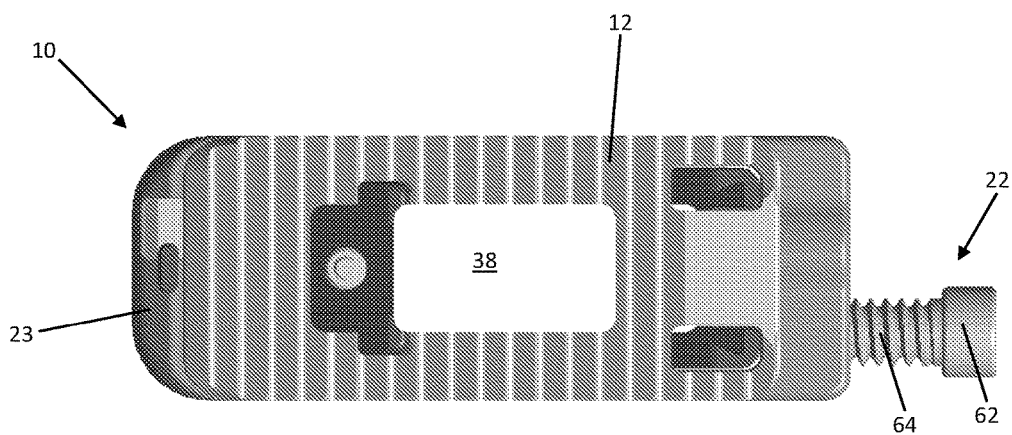
FIG. 3 is a top view of the expandable spinal fusion implant of FIG. 1.
Figure 4:
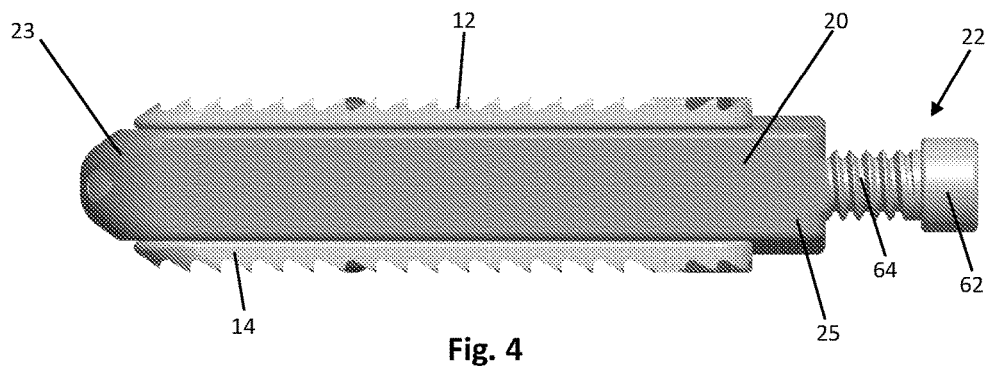
FIG. 4 is a side view of the expandable spinal fusion implant of FIG. 1 in its collapsed state.
Figure 5:
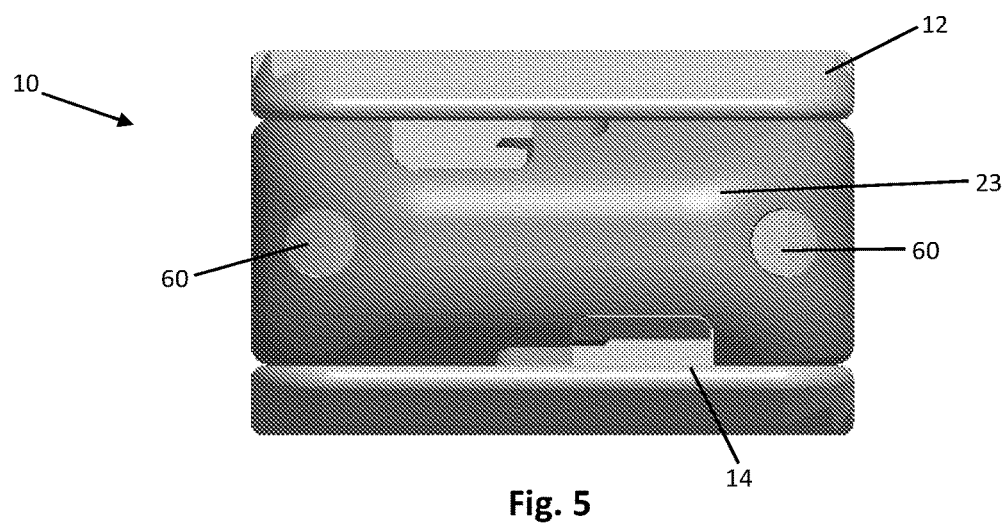
FIG. 5 is a leading end view of the expandable spinal fusion implant of FIG. 1 in its collapsed state.

FIGS. 1-13 illustrate an expandable spinal fusion implant for use during spinal surgery for implantation to an intervertebral disc space. According to an exemplary embodiment, the device is dimensioned for posterior approach surgery, e.g. posterior lumber interbody fusion (PLIF) and transforaminal lumbar interbody fusion (TLIF) approaches. However, according to an alternative embodiment, the device may also be dimensioned for use in a lateral approach to the anterior column of the spine. To reduce the risk of neural injury, the expandable spinal fusion implant has the ability to be implanted in a collapsed state (see FIG. 1) and expand to a height determined by the user (see FIG. 2). Expansion is accomplished by translating a wedge shaped expansion mechanism that is mated to the inferior and superior endplates 14, 12. As the expansion mechanism 26 is advanced towards the distal or leading end 16 of the implant 10 the endplates expand in height. To reduce the height of the implant or return the endplates back to their start position the expansion mechanism is advanced towards the proximal end of the device. In addition a large cannula at the trailing or proximal end of the device allows for post packing of bone graft material, i.e. filling the interior of the device with bone graft after the device has been inserted into the intervertebral space and expanded to the desired height. The ability to post pack improves the chances of a successful surgical outcome by allowing for insertion of a sufficient amount of bone graft in adequate contact with the vertebral body endplates adjacent the disc space to promote bone growth.

As shown in FIGS. 1-13, the expandable spinal fusion implant 10 has a top endplate 12 and a bottom endplate 14. The endplates 12, 14 have substantially identical features as will be further described. Each endplate has a bone contacting surface 46 and an interior surface 48. As shown in the exemplary embodiment, the bone contacting surfaces 46 may have anti-migration features 44. The interior surfaces 48 of the endplates 12, 14 have ramped portions 36 that correspond to the angles of the ramps 34, 35 on the expansion mechanism 26. The ramped portions 36 of the interior endplates also include a male dovetail feature 40 that mates with the female dovetail feature 38 on the ramps 34 of the expansion mechanism 26. Each endplate 12, 14 has a central fusion aperture 38 to allow for bone growth through the implant 10 and with the endplates of the adjacent vertebral bodies. In order for each endplate 12, 14 to expand it must remain stationary in the longitudinal axis as the expansion mechanism 26 translates both proximally and distally. Both endplates 12, 14 further include a distal extension 70 to aid in retaining the endplates within the housing 20. While the implant 10 according to an exemplary embodiment in FIGS. 1-13 is shown with flat endplates, endplates having built in lordosis, i.e. having a distal height extending from the bone contacting surface to the interior surface that is greater than the proximal height, are also contemplated.

The expandable spinal fusion implant 10 includes an expansion mechanism 26 located between the top and bottom endplates 12, 14. The expansion mechanism has two wedge portions 50, each of which as a superior ramp 34 and an inferior ramp 35 that correspond to and mate with the ramped portions 36, 37 of the superior and inferior endplates, respectively. Each endplate 12, 14 mates to the expansion mechanism 26 by an undercut or dovetail connection, at both the proximal end and the distal end, that allows movement between the wedge 50 and the endplate 12, 14. Each of the superior ramps 34 and inferior ramps 35 include a female dovetail feature 38 that mates with the male dovetail features 36 on the endplates 12, 14. An endplate safety retainer is housed within the expansion mechanism to prohibit removal of the endplates once assembled. The expansion mechanism 26 has a recess 56 at its proximal end dimensioned to receive the drive mechanism retainer 24 therein. The expansion mechanism 26 has a hollow interior defining a central fusion aperture 39 that aligns with the central fusion aperture 38 of the top and bottom endplates 12, 14 to allow for bone growth therethrough. The distal wedge 50 of the expansion mechanism 26 includes an endplate safety retainer 32 extending therethrough to prevent the dislocation of the endplates 12, 14 from the expansion mechanism 26.

Figure 6:
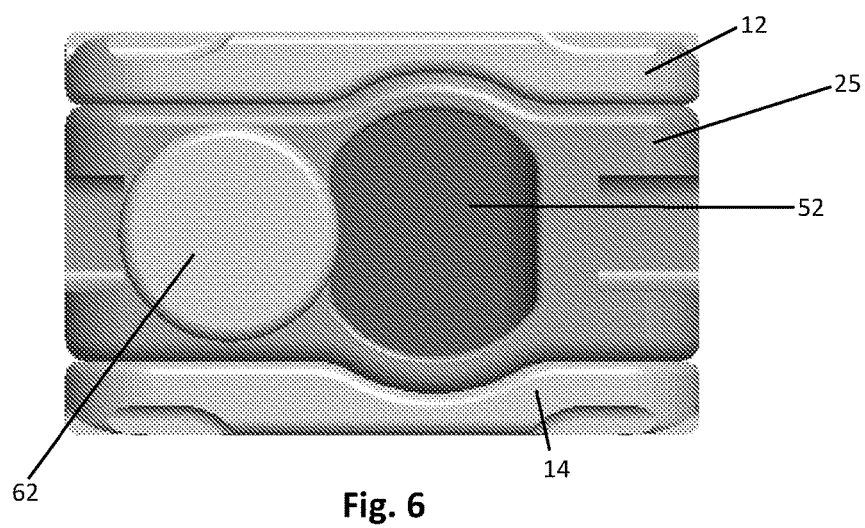
FIG. 6 is a trailing end view of the expandable spinal fusion implant of FIG. 1 in its collapsed state.
Figure 7:
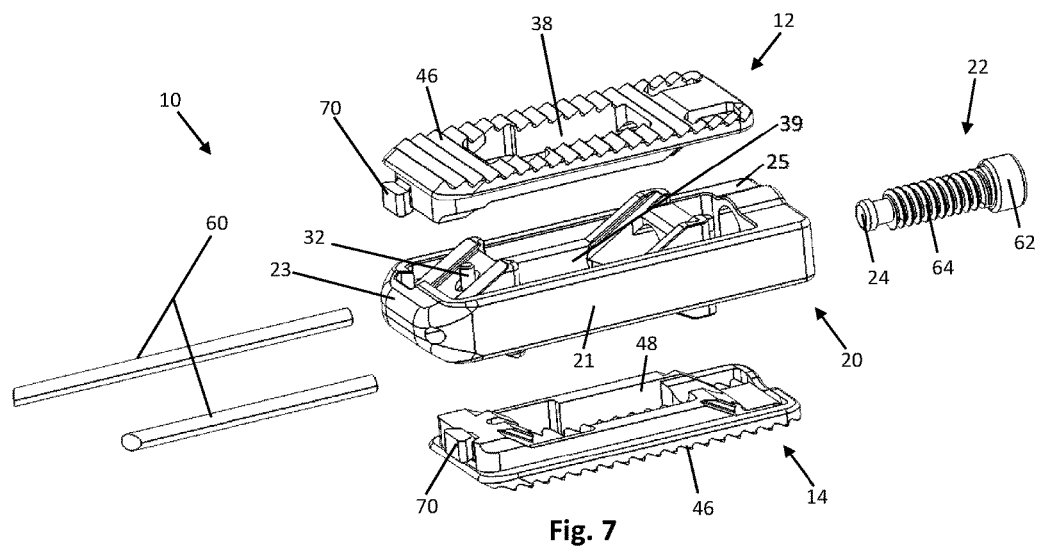
FIG. 7 is an exploded view of the expandable spinal fusion implant.
Figure 8:
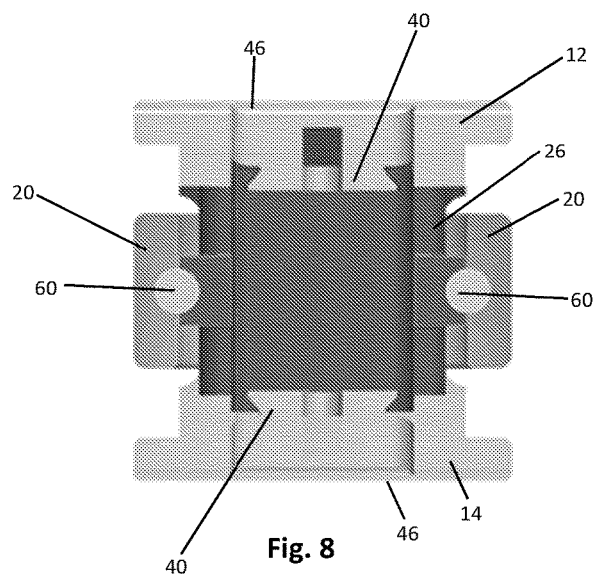
FIG. 8 is a cross sectional view of the leading end of expandable spinal fusion implant in its expanded state.
Figure 9:
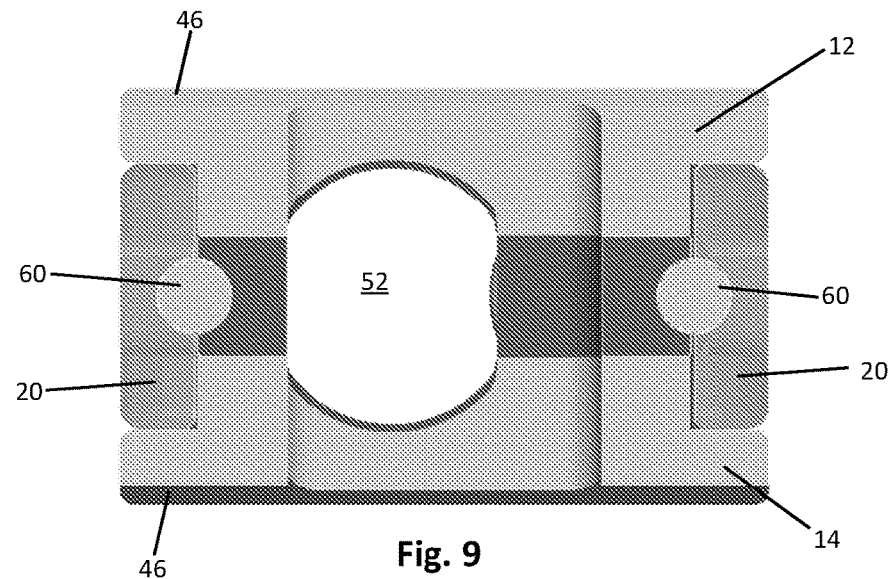
FIG. 9 is a cross sectional view of the trailing end of the expandable spinal fusion implant in its collapsed state.
Figure 10:
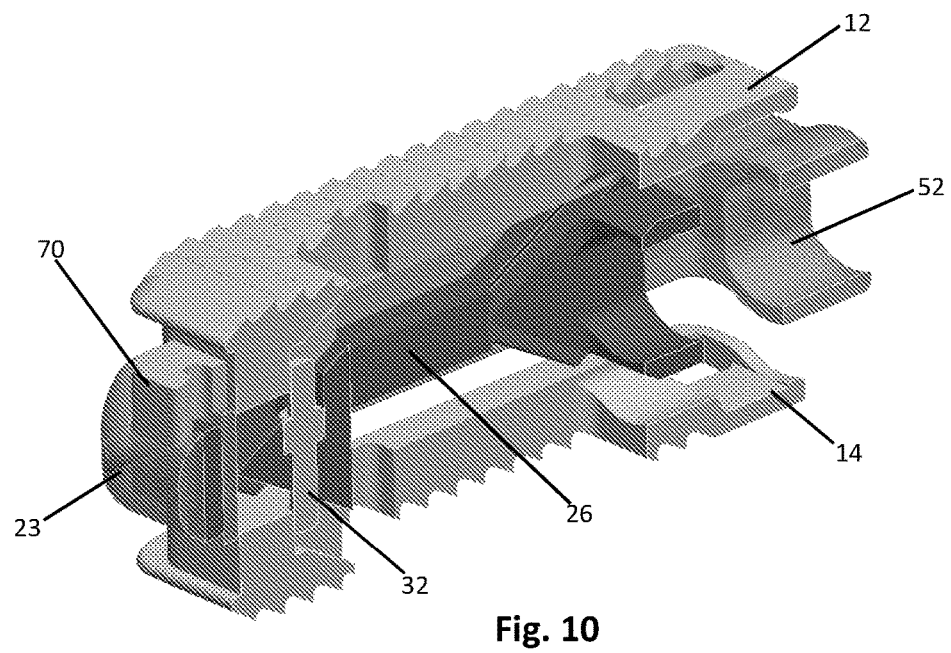
FIG. 10 is a cross sectional view of the expandable spinal fusion implant.
Figure 11:
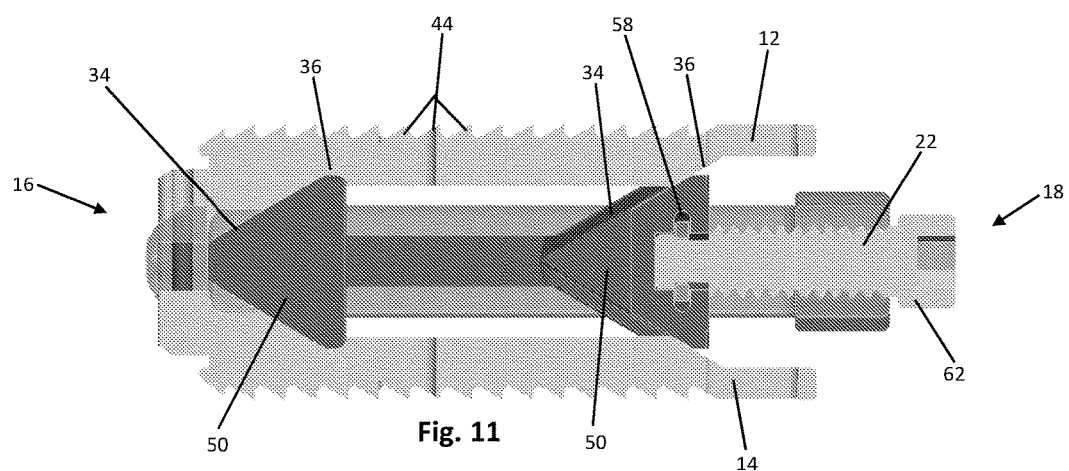
FIG. 11 is a cross sectional view of the expandable spinal fusion implant.
Figure 12:
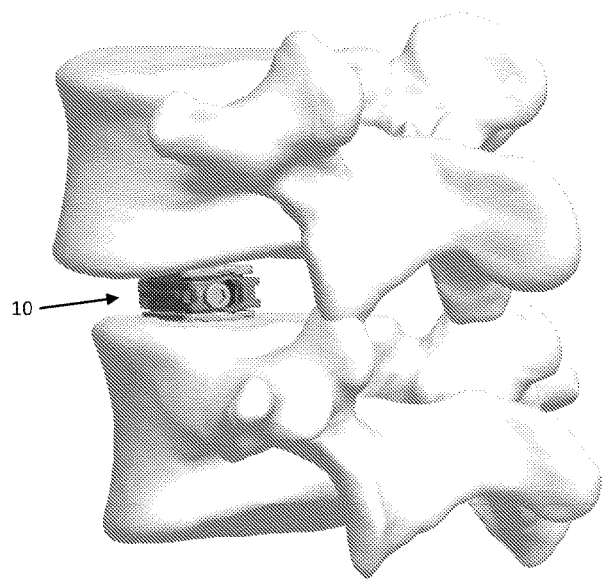
FIG. 12 is a perspective view of the expandable spinal fusion implant after insertion into the disc space.
Figure 13:
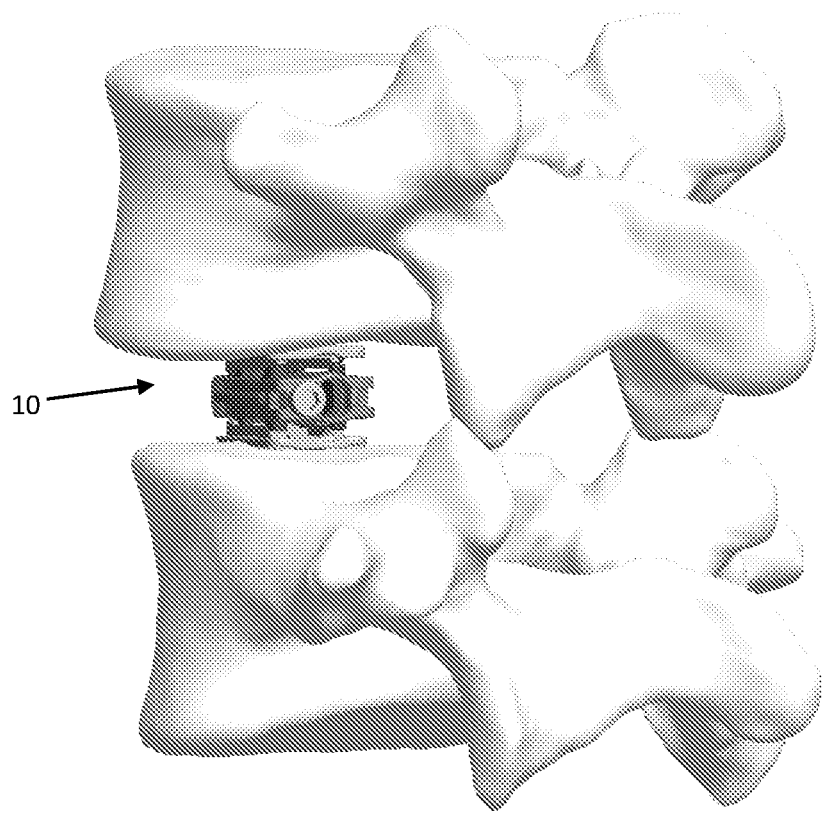
FIG. 13 is a perspective view of the expandable spinal fusion implant in its fully expanded state in the disc space.

As best shown in FIG. 7, the expandable spinal fusion implant 10 also includes a housing 20 dimensioned to house the expansion mechanism 26. The expansion mechanism 26 is supported in the housing 20 by two support rails 60. The housing 20 is defined by opposing lateral walls 21, a distal wall 23 and a proximal wall 25. The housing 20 has a longitudinal length that exceeds the longitudinal length of the endplates 12, 14. The distal wall 23 of the housing is tapered to aid in insertion of the implant 10. The distal wall 23 also includes recesses 58 for receiving the distal extensions 50 of the endplates 12, 14 to retain the endplates within the housing 20. As seen in FIG. 6, the proximal wall 25 of the housing 20 includes a cannula 52 for receiving bone graft material into the central fusion aperture 39 of the expansion mechanism 26 as well as a threaded drive mechanism aperture 54 for receiving the drive mechanism 22 therethrough.

According to the exemplary embodiment, the drive mechanism 22 has a head 62 at its proximal end for engaging an actuator tool (not shown) and a threaded shaft 64 extending from the head 62 and terminating at the distal end with a drive mechanism retainer 24 configured to anchor the drive mechanism 22 to the expansion mechanism 26. The purpose of the drive mechanism 22 is to translate the expansion mechanism 26 both proximally and distally. The threaded shaft 64 of the drive mechanism 22 engages with the threaded aperture 54 of the housing 20 at the proximal end 25 and also mates with the recess 56 at the proximal end of the expansion mechanism 26 and is retained with the expansion mechanism 26 by a drive mechanism retainer 24. As best seen in FIG. 6, the drive mechanism 22 is located at a position within the implant 10 that is offset from the central longitudinal axis of the implant 10 to allow for post packing of bone graft through the cannula 52 and into the central fusion aperture 39.

According to the exemplary embodiment, the expandable spinal fusion implant 10 is implanted into a patient by first accessing the desired intervertebral disc space via lateral approach to the anterior spinal column or a posterior (e.g. PLIF or TLIF) approach. The implant 10 is inserted in its collapsed state into the intervertebral disc space and maneuvered into a desired position. Once the desired position is reached, a tool is engaged with the drive mechanism 22 to turn the drive mechanism 22 and thereby urge the expansion mechanism 26 in the distal direction and consequently increase the distance between the top and bottom endplates 12, 14. The drive mechanism 22 can then be turned in the opposite direction to urge the expansion mechanism 26 in the proximal direction in order to decrease the distance between the endplates 12, 14 if necessary. Once the implant 10 has been set at the desired height, bone graft can be introduced through the cannula 52 in the proximal end 25 of the housing 20 to the interior of the implant 10, into the central fusion apertures 38, 39 of the expansion mechanism 26 and endplates 12, 14.

What is claimed is:

1. An expandable fusion implant, comprising:

first and second endplates each having a bone contacting surface and an interior surface with a central fusion aperture extending there between, the interior surface of each of the first and second endplates including a first and second ramped surface;

an expansion mechanism having a first and second wedge, each of the first and second wedges having a first ramp that engages the first and second ramped surfaces of the first endplate and a second ramp that engages the first and second ramped surfaces of the second endplate;

a housing defined by opposing lateral walls, a distal wall, and a proximal wall, the housing having a longitudinal length that is greater than a longitudinal length of the first and second endplates; and a drive mechanism having a head, a shaft extending from the head and terminating in a distal end, the shaft dimensioned to be received through an aperture in the proximal wall of the housing and the distal end configured to be received within a recess in the expansion mechanism, wherein rotation of the shaft in a first direction simultaneously drives both the first wedge and the second wedge toward the distal wall of the housing;

wherein the drive mechanism is offset from a width centerline extending from the proximal wall to the distal wall of the housing, wherein the housing has a cannula that is in communication with a central aperture in the expansion mechanism, and wherein the central aperture in the expansion mechanism is in communication with the central fusion apertures of the first and second endplates.

2. The expandable fusion implant of claim 1, wherein each of the first and second ramps of the first and second wedges faces at least partially toward the distal wall of the housing.

3. The expandable fusion implant of claim 2, wherein the first ramp of the first wedge engages the first ramped surface of the first endplate when the first wedge is distally advanced toward the distal wall, and the first ramp of the second wedge engages the second ramped surface of the first endplate when the second wedge is distally advanced toward the distal wall.

4. The expandable fusion implant of claim 1, wherein rotation of the shaft in a second direction simultaneously retracts both the first wedge and the second wedge away from the distal wall of the housing.

5. The expandable fusion implant of claim 1, wherein rotation of the shaft in the first direction advances the entire expansion mechanism toward the distal wall of the housing.

6. The expandable fusion implant of claim 5, wherein rotation of the shaft in a second direction retracts the entire expansion mechanism away from the distal wall of the housing.

7. The expandable fusion implant of claim 1, wherein the first wedge is fixedly secured relative to the second wedge, wherein the central aperture in the expansion mechanism is positioned between the first wedge and the second wedge.

8. An expandable fusion implant, comprising:
superior and inferior endplates each having a bone contacting surface and an interior surface with a central fusion aperture extending therebetween, the interior surface of each of the superior and inferior endplates including a distal and proximal ramped surface;
an expansion mechanism having a distal wedge and a proximal wedge and a central aperture, the distal wedge having a distal wedge superior ramp that engages the distal ramped surface of the superior endplate, the distal wedge having a distal wedge inferior ramp that engages the distal ramped surface of the inferior endplate, the proximal wedge having a proximal wedge superior ramp that engages the proximal ramped surface of the superior endplate, and the proximal wedge having a proximal wedge inferior ramp that engages the proximal ramped surface of the inferior endplate, wherein each of the distal wedge superior ramp, distal wedge inferior ramp, proximal wedge superior ramp, and proximal wedge inferior ramp faces at least partially toward the distal wall of the housing;
a housing defined by opposing lateral walls, a distal wall, and a proximal wall, the housing having a longitudinal length that is greater than a longitudinal length of the superior and inferior endplates; and
a drive mechanism having a head, a shaft extending from the head and terminating in a shaft distal end, the shaft dimensioned to be received through an aperture in the proximal wall of the housing, and the shaft distal end configured to engage the expansion mechanism and thereby cause movement of the distal wedge and proximal wedge;
wherein the drive mechanism is offset from a width centerline of the housing extending from the proximal wall to the distal wall of the housing, wherein the drive mechanism is configured to simultaneously advance the distal wedge and the proximal wedge toward the distal wall of the housing, wherein the housing has a cannula that is in communication with the central aperture in the expansion mechanism, and wherein the central aperture in the expansion mechanism is in communication with the central fusion apertures of the superior and inferior endplates.

9. The expandable fusion implant of claim 8, wherein the drive mechanism is configured to simultaneously retract the distal wedge and the proximal wedge away from the distal wall of the housing.

10. The expandable fusion implant of claim 8, wherein rotation of the shaft in a first direction advances both the distal wedge and the proximal wedge toward the distal wall of the housing.

11. The expandable fusion implant of claim 10, wherein rotation of the shaft in a second direction opposite to the first direction retracts the both the distal wedge and the proximal wedge away from the distal wall of the housing.

12. The expandable fusion implant of claim 8, wherein during simultaneous advancement of the distal wedge and the proximal wedge toward the distal wall, the distal wedge does not move with respect to the proximal wedge.

13. The expandable fusion implant of claim 8, wherein the expansion mechanism comprises an aperture in which the shaft distal end is positioned.

14. An expandable fusion implant, comprising:
superior and inferior endplates each having a bone contacting surface and an interior surface with a central fusion aperture extending therebetween, the interior surface of each of the superior and inferior endplates including a distal and proximal ramped surface;
an expansion mechanism having a distal wedge and a proximal wedge and an expansion mechanism central aperture, the distal wedge having a distal wedge superior ramp that engages the distal ramped surface of the superior endplate, the distal wedge having a distal wedge inferior ramp that engages the distal ramped surface of the inferior endplate, the proximal wedge having a proximal wedge superior ramp that engages the proximal ramped surface of the superior endplate, and the proximal wedge having a proximal wedge inferior ramp that engages the proximal ramped surface of the inferior endplate;
a housing defined by opposing lateral walls, a distal wall, and a proximal wall, the housing having a longitudinal length that is greater than a longitudinal length of the superior and inferior endplates; and
a drive mechanism configured to engage the expansion mechanism and thereby cause simultaneous and equal movement of both the distal wedge and the proximal wedge in a direction toward the distal wall; wherein the drive mechanism is offset from a width centerline of the housing extending from the proximal wall to the distal wall of the housing, and wherein the housing has a cannula that is in communication with the expansion mechanism central aperture;
wherein the expansion mechanism central aperture is in communication with the central fusion apertures of the superior and inferior endplates to thereby form a continuous and unobstructed opening which extends through the entire expandable fusion implant when viewed from a position superior to the superior endplate.

15. The expandable fusion implant of claim 14, wherein the drive mechanism comprises a head and a shaft, the shaft extending from the head and terminating in a shaft distal end, the shaft dimensioned to be received through an aperture in the proximal wall of the housing, and the shaft distal end configured to engage the expansion mechanism and thereby cause movement of the distal wedge and proximal wedge.

16. The expandable fusion implant of claim 15, wherein rotation of the shaft in a first direction advances both the distal wedge and the proximal wedge toward the distal wall of the housing.

17. The expandable fusion implant of claim 16, wherein rotation of the shaft in a second direction opposite to the first direction retracts both the distal wedge and the proximal wedge away from the distal wall of the housing.

18. The expandable fusion implant of claim 14, wherein each of the opposing lateral walls is substantially straight.

* * * * *